United States Patent
Speier et al.

(10) Patent No.: US 12,324,686 B2
(45) Date of Patent: Jun. 10, 2025

(54) METHOD AND SYSTEM FOR DETECTING MOVEMENT OF AT LEAST ONE PART OF A SUBJECT

(71) Applicant: Siemens Healthcare GmbH, Erlangen (DE)

(72) Inventors: Peter Speier, Erlangen (DE); Patrick Liebig, Erlangen (DE)

(73) Assignee: Siemens Healthineers AG, Forchheim (DE)

( * ) Notice: Subject to any disclaimer, the term of this patent is extended or adjusted under 35 U.S.C. 154(b) by 325 days.

(21) Appl. No.: 17/742,388

(22) Filed: May 11, 2022

(65) Prior Publication Data

US 2022/0361822 A1 Nov. 17, 2022

(30) Foreign Application Priority Data

May 12, 2021 (EP) .................................. 21173644

(51) Int. Cl.
*A61B 5/00* (2006.01)
*A61B 5/055* (2006.01)
(Continued)

(52) U.S. Cl.
CPC .............. *A61B 5/721* (2013.01); *A61B 5/055* (2013.01); *G01R 33/3415* (2013.01);
(Continued)

(58) Field of Classification Search
CPC ....... A61B 5/721; A61B 5/055; A61B 5/1126; A61B 5/7214; G01R 33/3415;
(Continued)

(56) References Cited

U.S. PATENT DOCUMENTS

2016/0245888 A1 8/2016 Bollenbeck
2017/0160364 A1 6/2017 Fenchel
(Continued)

FOREIGN PATENT DOCUMENTS

| EP | 3742184 A1 | 11/2020 | |
|---|---|---|---|
| WO | 2018173009 A1 | 9/2018 | |
| WO | WO-2020234207 A1 * | 11/2020 | ............. A61B 6/037 |

OTHER PUBLICATIONS

Jaeschke, Sven HF, Matthew D. Robson, and Aaron T. Hess. "Scattering matrix imaging pulse design for real-time respiration and cardiac motion monitoring." Magnetic resonance in medicine 82.6 (2019): 2169-2177.

*Primary Examiner* — Peter Luong
(74) *Attorney, Agent, or Firm* — Lempia Summerfield Katz LLC

(57) ABSTRACT

Movement detection of at least one part of a subject located inside a magnetic resonance imaging (MRI) device is provided. A method includes performing an MR scan by executing a programmable MR sequence protocol. The sequence protocol includes MR excitation pulses to be transmitted via a parallel transmit system and receive time windows for receiving magnetic resonance signals via a receive system. The MR sequence protocol includes, in between the MR excitation pulses, the generation of multi-channel pilot tone signals that are transmitted via the parallel transmit system and an RF transmit coil array. During transmission of the multi-channel pilot tone signals, the pilot tone signals are received with an RF receive coil array. The received pilot tone signals are forwarded via the receive system to an analyzing unit, and movement of at least one part of the subject is determined by analyzing the received pilot tone signal.

18 Claims, 4 Drawing Sheets

(51) Int. Cl.
  *G01R 33/3415*  (2006.01)
  *G01R 33/36*  (2006.01)
  *G01R 33/54*  (2006.01)
  *G01R 33/565*  (2006.01)
  *G01R 33/567*  (2006.01)

(52) U.S. Cl.
  CPC ....... *G01R 33/3621* (2013.01); *G01R 33/543* (2013.01); *G01R 33/56509* (2013.01); *G01R 33/5673* (2013.01)

(58) Field of Classification Search
  CPC ............ G01R 33/36221; G01R 33/543; G01R 33/56509; G01R 33/5673; G01R 33/288; G01R 33/36; G01R 33/5612
  See application file for complete search history.

(56) References Cited

U.S. PATENT DOCUMENTS

| | | |
|---|---|---|
| 2017/0160367 A1* | 6/2017 | Schröter .......... G01R 33/56509 |
| 2018/0045801 A1 | 2/2018 | Speier |
| 2018/0353139 A1 | 12/2018 | Speier |
| 2018/0353140 A1 | 12/2018 | Speier |
| 2019/0298217 A1 | 10/2019 | Speier |
| 2019/0377051 A1 | 12/2019 | Bacher et al. |
| 2020/0166597 A1 | 5/2020 | Speier et al. |
| 2020/0375463 A1 | 12/2020 | Hess et al. |

* cited by examiner

METHOD AND SYSTEM FOR DETECTING MOVEMENT OF AT LEAST ONE PART OF A SUBJECT

This application claims the benefit of European Patent Application No. EP 21173644.2, filed on May 12, 2021, which is hereby incorporated by reference in its entirety.

BACKGROUND

The present embodiments relate to a method for detecting movement of at least one part of a subject, a system for detecting movement of at least one part of a subject, and a corresponding computer program.

Patient movement during a diagnostic examination or scan of medical data often causes artefacts in the acquired images. Magnetic Resonance (MR) imaging is relatively slow, so that respiratory, cardiac, and/or other movement will occur during the scan. Therefore, the data acquisition may be synchronized with any movement that may affect a medical image during the whole time of the examination.

A way for gaining information about movement during data acquisitions in MR measurements is achieved by inducing coherent and/or continuous electromagnetic radio frequency (RF) signals that are close to but outside the frequency band of the RF signals used for the MR imaging (e.g., the Larmor frequency). These RF signals are referred to as pilot tone (PT) signals. The advantage of such a pilot tone navigation in MR is the possibility to utilize the receive subsystem of the MR system in order to detect variations in the PT signal that are induced by movement of the patient. Hence, the PT signal may be placed at a frequency outside the band occupied by the MR signal but still inside the frequency band detected by the MR receiver. Nevertheless, additional signal generation hardware, such as a conductor loop and corresponding signal generating electronics, is still to be provided in order to generate the PT. The amount of required hardware may typically scale with the number of PT signals to be generated.

Another approach is proposed by Jaeschke et al. (Jaeschke et al.: "Scattering matrix imaging pulse design for real-time respiration and cardiac motion monitoring," Magn Reson Med. 2019; 82:2169-2177), where special RF pulses with individual signature on each element of a transmit array are sent and the reflected signal is measured with a scanner built-in transmit monitoring system in all elements. Thus, using a variety of RF pulse distributions to the array elements, the couplings between all elements may be resolved. The drawback of this method is the use of the transmit monitoring system to detect the coupling. The method requires sending RF signals of substantial energy for every PT measurement time point. Thus, this system is typically not usable for monitoring patients when there is no RF applied (e.g., between scans or for sequences with longer gaps).

SUMMARY AND DESCRIPTION

The scope of the present invention is defined solely by the appended claims and is not affected to any degree by the statements within this summary.

The present embodiments may obviate one or more of the drawbacks or limitations in the related art. For example, a way of monitoring that allows movement detection of a subject or patient being imaged in a magnetic resonance imaging device as reliably and continuously as possible while requiring as little additional hardware as possible is provided.

According to a first aspect, a method for detecting movement of at least one part of a subject being located inside a magnetic resonance (MR) imaging device is provided. The magnetic resonance imaging device includes a parallel transmit system having multiple channels, that is configured to transmit magnetic resonance excitation pulses via an RF transmit coil array, and a receive system (e.g., a parallel receive system having multiple channels) that is configured to receive magnetic resonance signals via an RF receive coil (e.g., an RF receive coil array).

The method includes performing a magnetic resonance scan by executing a programmable magnetic resonance sequence protocol. The sequence protocol includes magnetic resonance excitation pulses to be transmitted via the parallel transmit system as well as receive time windows for receiving magnetic resonance signals via the receive system. The magnetic resonance sequence protocol includes, in between the magnetic resonance excitation pulses, the generation of multi-channel pilot tone signals that are transmitted via the parallel transmit system and the RF transmit coil array. During the transmission of the multi-channel pilot tone signals, the pilot tone signals are received with the RF receive coil. The received pilot tone signals are forwarded via the receive system to an analyzing unit. Movement of at least one part of the subject is determined by analyzing the received pilot tone signal at the analyzing unit.

The subject may, for example, be a human or animal subject (e.g., a patient). A part of a subject may, for example, be a body part of the human or animal body subjected to motion. The body part may be the head or part of the head, a part of the respiratory system (e.g., the lung or the patient's chest or thorax), a part of the cardiac system (e.g., the heart), a blood vessel or other parts that are affected by the pulsatile arterial blood flow, or any other organ or body part affected by motion, such as an extremity (e.g., a knee, leg or part thereof, foot, arm, hand etc.). For example, the part of the subject may be undergoing or may be affected by a cyclical movement (e.g., cardiac or respiratory movement). Located inside a magnetic resonance imaging device may, for example, be that the at least one part of the subject is located inside the sensitive area of such MRI device (e.g., inside the bore of a main magnet). The part of the subject may further be inside the sensitive area of a local RF coil (e.g., an RF coil that is to be placed close to the part of the body from which images are to be acquired), which may include the RF transmit coil array. A detected movement may be a natural and unavoidable movement caused, for example, by breathing or heartbeat, but also voluntary and/or involuntary movements of the subject or body parts caused, for example, by anxiety or impatience, such as a movement of the head or extremities. Alternatively and/or additionally, a detected movement may be a requested/instructed intentional motion that is part of the exam (e.g., bending the knee for a dynamic study of the joint motion or instructed breathing).

The parallel transmit system has multiple channels and is adapted to transmit magnetic excitation pulses via the RF transmit coil array. The term "parallel" in parallel transmit system may be that the channels of such a system are active simultaneously. For example, a number of signals may be transmitted in parallel (e.g., at the same time). In one embodiment, parallel may not be such that the transmit system and the receive system are active at the same time. Hence, the parallel transmit system may, for example, be configured to produce a number of individual magnetic fields or subfields via the multiple channels. By time-controlling the generation of the fields, the magnetic resonance excitation pulses may be generated having determined signal characteristics, such as frequency, phase, and/or amplitude. The multiple channels may each be powered and controlled independently (e.g., such that each individual transmit coil of the RF transmit coil array may be operated via an individual channel of the multiple channels). The RF transmit coil array may be a coil that is applicable for at least one body region (e.g., a head coil, a knee coil, or a flexible array coil, such as used for imaging of abdomen or thorax). In other words, a local coil may be placed close to the body region from which MR images are to be acquired. The receive system may be a one-channel system. In one embodiment, the receive system is a parallel receive system and may have multiple channels. The term "parallel" in parallel receive system may be that the channels of such a system are active simultaneously. For example, a number of signals may be received in parallel (e.g., at the same time). For example, each channel may acquire a separate signal component (e.g., the raw data signal may include a number of, possibly complex, signal components). Each signal component may be picked up by an element of a receive coil array. For example, the parallel transmit system and/or the parallel receive system may have 4-128 (e.g., 8-64) channels. In one embodiment, the RF receive coil or coil array and the RF transmit coil array may be integrated in one RF transceiver array, where the transceiver array includes both transmit coils and RF receive coils. Alternatively, the RF receive coil array and the RF transmit coil array may be separate. For example, the RF transmit coil array and/or the RF receive coil array may each include 4-32 coils (e.g., 8 coils). In one embodiment, the transmit system and the receive system of the measurement system of the MR device may be used to generate and detect the pilot tone signal. Receive coils of the receive coil array and transmit coils of the transmit coil array may be placed in various predetermined locations in order to achieve a more reliable and complete detection of movement. Therefore, no additional hardware may be needed in order to realize the method of one or more of the present embodiments.

The pilot tone signals may be applied in between the magnetic resonance excitation pulses throughout the complete magnetic resonance sequence protocol. Alternatively, the pilot tone signals may be applied only at one or a number of stages or time intervals of the protocol. Additionally or alternatively, the pilot tone signals may be applied in between MR measurements (e.g., in order to keep track of movement in between the measurements). An MR sequence protocol generally includes excitation time windows, during which MR excitation pulses are transmitted. During this time, no signal is received. This is often followed by a "free" window, during which neither MR excitation pulses are transmitted nor MR signals are received. Generally, the MR-signal is manipulated or position encoded via gradient pulses during the "free" windows. Finally, an MR signal (e.g., a gradient or spin echo) is received during one or a number of receive time windows. The pilot tone signals may be generated all the time, and may be received for the whole time when the receiver is "open", even during the receive time window. However, the pilot tone signals cannot be received during the excitation time window, when the receiver is detuned or "closed" because of the high amplitude of the MR excitation pulses. The amplitude of the pilot tone signal during the excitation time window may be zero. However, the amplitude may be non-zero, but the amplitude is not recorded at the receive elements. In one embodiment, the amplitude of the pilot tone signal is limited and/or reduced during the receive time window. An overview of the time windows may be as follows:

| Time window | Receiving possible | PT amplitude |
| --- | --- | --- |
| excitation time window | No | any (may be zero) |
| free time window | Yes | high |
| receive time window | yes | limited/lower |

Alternatively or additionally, the pilot tone may not be generated during the receive time windows. According to an embodiment, the amplitude of the pilot tone signal may be lowered during the receive time windows. In other words, the amplitude of the pilot tone signal may be zero during MR excitation pulses and higher than zero in between MR excitation pulses. The amplitude of the pilot tone signal may further have a first value in between receive time windows and a second value during receive time windows. The first value is greater than the second value (e.g., the first value may be at least two times greater than the second value). Such timing may prevent the receive system from being overdriven and/or being used in a non-linear region due to receiving the magnetic resonance signals and the pilot tone signals at the same time. Typically, the time occupied by transmitting RF pulses during a scan may only be a small fraction of the whole scan time. Accordingly, the option to detect in between MR excitation pulses may basically allow to detect movement nearly all the time during the scan and may thus greatly increase the quality of the data. At the same time, using the parallel transmit system of the MR device may allow to generate multiple parallel pilot tone signals, where the quality and richness of the pilot tone information may be increased while only using existing hardware of the MR device.

The pilot tone signal may be generated via any periodic oscillating electronic (e.g., a sine wave or a square wave), or the pilot tone signal may be based on such a signal (e.g., a modulated signal). The frequency of the pilot tone signal may, for example, be in the radio frequency (RF) range (e.g., 1 MHz-500 MHz). In one embodiment, the pilot tone signal may be transmitted in a continuous wave mode. The generation of multi-channel pilot tone signals may be understood in the sense that a number of pilot tone signals are created at different channels of the parallel transmit system. For example, a control unit may control at least some of the channels of the parallel transmit system in order to cause the generation and transmission of parallel pilot tone signals. The different pilot tone signals may either be generated in parallel or consecutively. The pilot tone signal and/or the RF coupling between the RF transmit coil array and the RF receive coil array may be modulated by the subject or by the at least one part of the subject. Also, the movement may induce changes in the load of the RF coils (e.g., the RF receive coil array), and the changes may be detected when analyzing the received pilot tone signal. The reception of the pilot tone signals may also be controlled by the control unit (e.g., by controlling at least some of the channels of the MR receive system). The pilot tone signal modulation may, for example, be due to eddy currents induced in the subject by the pilot tone signal. These eddy currents may in turn influence pilot tone signal and/or the coupling between the transmit system and the receive system. For example, the modulation of the pilot tone signal may be changed due to movement of the at least one part of the subject (e.g., a different positioning of the at least one part of the subject may influence the induction of eddy currents and/or the influence the eddy currents have on the signal transmission between the transmit system and the receive system). For example, changes of the pilot tone signal may include changes in the amplitude and/or phase. Hence, the movement may influence the signal transmission between the transmit system and the receive system.

The analysis unit may be any digital processing system (e.g., a CPU) and may be, for example, on any computer or laptop or tablet. The analyzing unit may be part of the magnetic resonance system or the magnetic resonance device (e.g., a control unit or computer associated with the MR imaging device). Additionally and/or alternatively, the received pilot tone signal may be forwarded to an analyzing unit outside the magnetic resonance system (e.g., to a remote server or computer that includes the analyzing unit via a network or via Internet). The analyzing unit may determine movement, for example, by detecting changes in the transmitted pilot tone signal and thereby deducing the movement of the subject. A movement of the subject may, for example, be detected if the phase and/or amplitude of the transmitted pilot tone signal changes beyond a pre-determined threshold. Data processing may be trained based on a training dataset. The training dataset may be based on previous measurements with different subjects in similar geometries (e.g., via practice measurements with guided and/or predetermined movements) or on electromagnetic simulations. For example, the training may be used to determine the effect of movement on the signal. A pre-determined threshold may, for example, be set for a movement that is just tolerable in terms of disturbance of the MR measurement. The dataset may be taken continuously in case of continuous movements, such as movements based on breathing and/or heartbeat. The transmitted pilot tone signal may, for example, be a continuous signal of constant frequency, and the received pilot tone signal may be observed for changes in itself (e.g., over time, such as by constantly monitoring frequency, phase, and/or amplitude), and observing if any of these parameters change, for example, by at least a pre-determined threshold within a pre-determined time window. Alternatively, the received pilot tone signal may be compared with the transmitted pilot tone signal (e.g., initial pilot tone signal) to thereby detect any changes above at least one pre-determined threshold. Detected changes may then be used to determine the movement (e.g., by comparing changes detected via different channels and/or via different receive coils of the receive coil array).

According to an embodiment, the frequency of the pilot tone signal may be outside the frequency band of the RF imaging pulses. For example, the frequency of the pilot tone signal may be 20 to 500 kHz or 50 to 200 kHz away from the center frequency of the RF imaging pulses. If the system allows a larger distance from the central frequency (e.g., if the bandwidth of the receive elements and the position of the MR signals in the receiving band is appropriate), a larger distance may be advantageous. For example, the frequency of the pilot tone signal may be between 500 kHz and 2 MHz away from the center frequency of the RF imaging pulses. The frequency being outside the frequency band may help to avoid interference with the Magnetic Resonance imaging data. The frequency may still be inside the bandwidth of the receive and transmit system, such that the MR hardware may be used to generate and receive the pilot tone signal.

According to an embodiment, the pilot tone signals may have an amplitude that is significantly smaller (e.g., 100 to 5000 times smaller or 1000 to 3000 times smaller) than the amplitude of an average magnetic resonance excitation pulse. A low amplitude of the pilot tone signals may provide that the pilot tone signal does not overdrive the receive system. For example, the amplitude of an electronically generated pilot tone signal in the transmit system may be in the range of 0.01V to 2V (e.g., 0.05V to 0.15V). The amplitude of a typical magnetic resonance excitation pulse may be in the range of 100V to 300V (e.g., 200V). In one embodiment, a small amplitude of the pilot tone signal may provide that the signal to noise ratio of the MR measurement is not hampered. In one embodiment, the signal path in the parallel transmit system is linear at small signal amplitudes. Thus, the generation of low energy (e.g., low amplitude) pilot tone signals is enabled without needing an additional generator loop for the generation of the pilot tone signal. Further, a low amplitude of the pilot tone signal may, for example, allow for the pilot tone to be generated continuously throughout an exam and, thus, to monitor the subject not only during scans, but for the whole exam.

According to an embodiment, the pilot tone signals may be created (e.g., generated) in multiple parallel transmit channels. Signal characteristics (e.g., frequency, phase, and/or amplitude) are modulated for each transmit channel separately in order to create various pilot tone signals with different signal characteristics. For example, the pilot tone signals may be transmitted via different local transmit coils. Transmitting pilot tone signals via different local transmit coils may lead to a more distinct spatial transmit variation, and thus, for example, to a more distinct and/or versatile detection of movement. In one embodiment, the MR transmit system may typically be fully programmable and provide various possibilities to adjust the signal characteristics natively. Hence, an adjustment of the hardware may not be necessary in order to allow for a configuration. The signal characteristics of multiple pilot tone signals may be adjusted individually. The adaption of signal characteristics may, for example, be used to optimize the detection of predetermined movements of parts of the subject, such as of movement of a head (e.g., nodding, turning of the head).

According to an embodiment, multiple pilot tone signals may be transmitted in parallel via the RF transmit coil array. The multiple pilot tone signals differ in frequency. Different frequencies for individual pilot tone signals may, for example, be used to distinguish and/or separate the different pilot tone signals at the receiver side. A parallel sending (e.g., transmission) of pilot tone signals may provide a higher signal quality and/or a reduced system complexity. In one embodiment, the receive system may include multiple receive routines (e.g., multiple parallel electronic signal processing components, such as one for each pilot tone frequency) in order to process the multiple pilot tone signals simultaneously.

Alternatively and/or additionally, different pilot tone signals may be transmitted consecutively via the different channels of the parallel transmit system. The pilot tone signals may be separated at the receiver system side by analyzing at least one of their signal characteristics (e.g., their phase). Correspondingly, the different pilot tone signals may differ in at least one signal characteristic. Consecutively sending different pilot tone signals may allow to distinguish different signals without having to rely on the application and detection of different frequencies. Thus, multiple receive routines may not be required. For example, a field programmable gate array (FPGA) used for signal processing may be limited in space, and therefore, multiple signal processing (e.g., receive) routines may not be applicable in all cases or may be difficult to implement. According to an embodiment, the signal characteristics of the modulated pilot tone signals may be shared between the parallel transmit system and the receive system. Sharing information about signal characteristics may enable a reliable way of signal recognition.

According to an embodiment, at least two pilot tone signals may be transmitted from two transmit coils at opposing sides of the subject, both transmit coils being part of the RF transmit coil array. The at least two pilot tone signals are modulated such that their interference pattern has at least one constant minimum at one part of the subject, from which movement is not to be taken into account. For example, a stationary wave may be created with the at least two pilot tone signals, where the nodes (e.g., absolute minima) of the wave are located at a position that is not to be taken into account for movement detection (e.g., due to not being relevant). Such a stationary wave may be insensitive to at least one area and particularly sensitive in other areas. For example, when examining a head of a patient, the movement of the mouth (e.g., swallowing movement) may be disregarded for movement detection if the mouth is not relevant for the measurement.

According to an embodiment, a specific adsorption rate (SAR) supervision of the subject may be replaced by adding a constant safety factor within a general SAR model instead of a measured SAR. A specific adsorption rate of the subject (e.g., due to the pilot tone signal) may be calculated by adding a constant safety factor within a general SAR model. The SAR of a subject (e.g., a patient) may usually be determined by measuring the reflected power during the transmission of MR excitation pulses. Due to hardware restrictions (e.g., using the same hardware; cable) for the received signal at the receive system and the reflected power at the transmit system, it may not be possible to receive a reflected power of the magnetic resonance excitation pulses and from the receivers at the same time. Hence, the application of the pilot tone signal may prevent a simultaneous SAR supervision. This problem may be overcome by adding a constant safety factor to the SAR determined for the MR excitation pulses. This results in a loss in accuracy below 1%. This is possible because the SAR for the pilot tone signal is in such a small range.

According to an embodiment, the method may include the additional act of receiving the signal reflected during a magnetic resonance excitation pulse via the parallel transmit system and separating the reflected signal from the magnetic resonance excitation pulse being currently transmitted by at least one directional coupler. The method may also include the additional act of forwarding the reflected signals to the receive system and further to the analysing unit. The method may also include determining movement of the subject during transmission of the magnetic resonance excitation pulse by analyzing changes in the reflected signal at the analyzing unit. Accordingly, the movement detection may be realized during the whole time on an exam (e.g., in between MR excitation pulses and during MR excitation pulses). Hence, a more time complete detection of movement may be possible. Typically, the generation of MR excitation pulses via forwardly directed signals may lead to a fraction of the signals being backscattered, which leads to a superposition of forward running signal components or waves and backwards running signal components or waves in the signal generation electronics. The amount and/or characteristics of the backwards running signal components may depend on the subject and a position of the subject with relation to the RF transmit coils. Hence, changes of the backward running signal (e.g., reflected signal) may give information about the position and movement of the at least one part of the subject.

For the purpose of movement detection, a motion detection pulse may be added to the MR excitation pulse, where the motion detection pulse may, for example, have a slightly different frequency than the MR excitation pulse. Alternatively or additionally, the motion detection pulse may have a smaller amplitude than the MR excitation pulse. The different frequency may allow to distinguish the motion detection pulse and the corresponding backscattered signal from the MR excitation pulse. There may be one directional coupler for each channel of the parallel transmit system. The at least one directional coupler may, for example, be a circulator. The at least one directional coupler (e.g., a circulator) may decouple the different pulses (e.g., by separating a forward wave, such as the outgoing MR excitation pulse, from the backwards wave, such as the reflected signal). The reflected signals may be forwarded to the same signal path as the signals from the receive system via a switch.

According to an embodiment, the movement may be determined by using a scatter matrix for analysing the received pilot tone signals. The scatter matrix may contain all possible couplings between coil elements. As such, the scatter matrix may, for example, be a complete description of the input data for the analysis of the received signals. The received pilot tone signals $V_{i,j,rec}$ may be identified on each channel, where the received pilot tone signals may correspond to the transmitted pilot tone signals $V_{j,tra}$ via the scatter matrix $S_{i,j}$:

$$V_{i,j,rec} = S_{i,j} V_{i,j,tra}$$

The scatter matrix $S_{i,j}$ may, for example, be time dependent and divided into a number of components, such as a static term representing the properties of the coils, and terms representing movement of the subject or of one or a number of parts of the subject. The evaluation via the scatter matrix may, for example, be carried out analogously to the method described by Jaeschke et al. (see Jaeschke et al.: "Scattering matrix imaging pulse design for real-time respiration and cardiac motion monitoring", Magn Reson Med. 2019; 82:2169-2177).

According to another aspect, a magnetic resonance imaging system configured to detect movement of at least a part of a subject is provided. The part of the subject is located inside an examination area of the magnetic resonance imaging system. The system includes a parallel transmit system having multiple channels that is configured to generate and transmit magnetic resonance excitation pulses via an RF transmit coil array, and a receive system (e.g., a parallel receive system having multiple channels) that is configured to receive magnetic resonance signals via an RF receive coil array. The system also includes a control unit including an analysing unit. The control unit is configured to prompt the parallel transmit system to generate and transmit pilot tone signals according to sequence protocol in between the transmission of magnetic resonance excitation pulses, and to prompt the receive system to receive pilot tone signals and forward the received pilot tone signals to the analyzing unit. The analyzing unit is configured to determine movement of the subject by analyzing changes in the received pilot tone signal. All features and advantages of the method may be adapted to the system and vice versa.

According to an embodiment, the signal path in the parallel transmit system may be linear at small signal amplitudes (e.g., at signal amplitudes of about 0.01V to 1V or 0.02V to 0.5V). The given values may correspond to the amplitudes generated in the signal generating electronics of the transmit system. The signal path being linear at small amplitudes may allow to prevent overdriving of the receive elements of the receive system by enabling the generation of pilot tone signals with correspondingly small amplitudes and/or energy. For example, the small signal amplitudes may be 100 to 5000 times smaller or 1000 to 3000 times smaller than the signal amplitude of the average MR excitation pulses. The average MR excitation pulses may, for example, have an amplitude of about 100V to 300V (e.g., 200V).

According to an embodiment, the RF transmit coil array and the RF receive coil array may be integrated into one local coil that is configured to be placed close to the part of the subject inside the magnetic resonance imaging device. The one local coil may thus be a transceiver coil, where some of the transceiver elements are used for signal transmission and some of the transceiver elements are used for signal reception. This embodiment may allow a particularly compact and/or space-saving design. Alternatively, the pilot tone signal may be transmitted with a body coil.

According to an embodiment, the magnetic resonance imaging system may operate at about 7 Tesla. Systems operating at 7 Tesla are often provided without a body coil but with several local coils, since the required power for such 7T systems with a body coil may be too high to be feasible in many cases. Accordingly, systems operating at 7 Tesla may be particularly well adapted to be used with the present embodiments due to natively including local coils. The use of local coils instead of a body coil for transmitting the pilot tone signal may also be decreasing power consumption.

According to an embodiment, the signal generating elements may include at least one directional coupler, where the at least one directional coupler is configured to separate incoming signals that are incoming at the RF transmit coil array and outgoing signals that are currently transmitted from the RF transmit coil array, and forward the incoming signals to the receive system. The at least one directional coupler (e.g., at least one circulator) may be configured to decouple the different pulses (e.g., by separating a forward wave, such as the outgoing MR excitation pulse) from the backwards wave (e.g., the reflected signal). The receive system may include a switch and be configured to forward reflected signals to the same signal path as the signals from the receive system via the switch. For example, the receive coil array and the transmit coil array or at least one receive coil and at least one transmit coil may share a signal line for forwarding both the received signals that are incoming at the receive system and at the transmit system.

According to another aspect, a computer program including programming code is provided. The programming code causes a control unit connected to a magnetic resonance imaging device or being part of a magnetic resonance imaging device to carry out the method as described herein when the programming code is executed on the control unit. All features and advantages of the method and of the system may be adapted to the computer program and vice versa. The computer program may, for example, be configured to be started and terminated by a user. Further, the computer program may be configured such that a number of input parameters may be entered by a user to optimize the output of the method.

According to another aspect, a non-transient digital storage medium containing the computer program as described above is provided. All features and advantages of the method, of the system, and of the computer program may be adapted to the digital storage medium (e.g., a non-transitory computer-readable storage medium) and vice versa. The digital storage medium may be in form of a hard drive, such as a magnetic hard disk or a solid-state drive, in form of a portable storage medium such as a CD, DVD, or USB-Stick, or in form of a network storage medium, such as a cloud storage.

Another aspect is a control unit configure for performing the method as described, where the control unit may be part of a computer and/or part of a magnetic resonance system.

DETAILED DESCRIPTION

Figure 1:
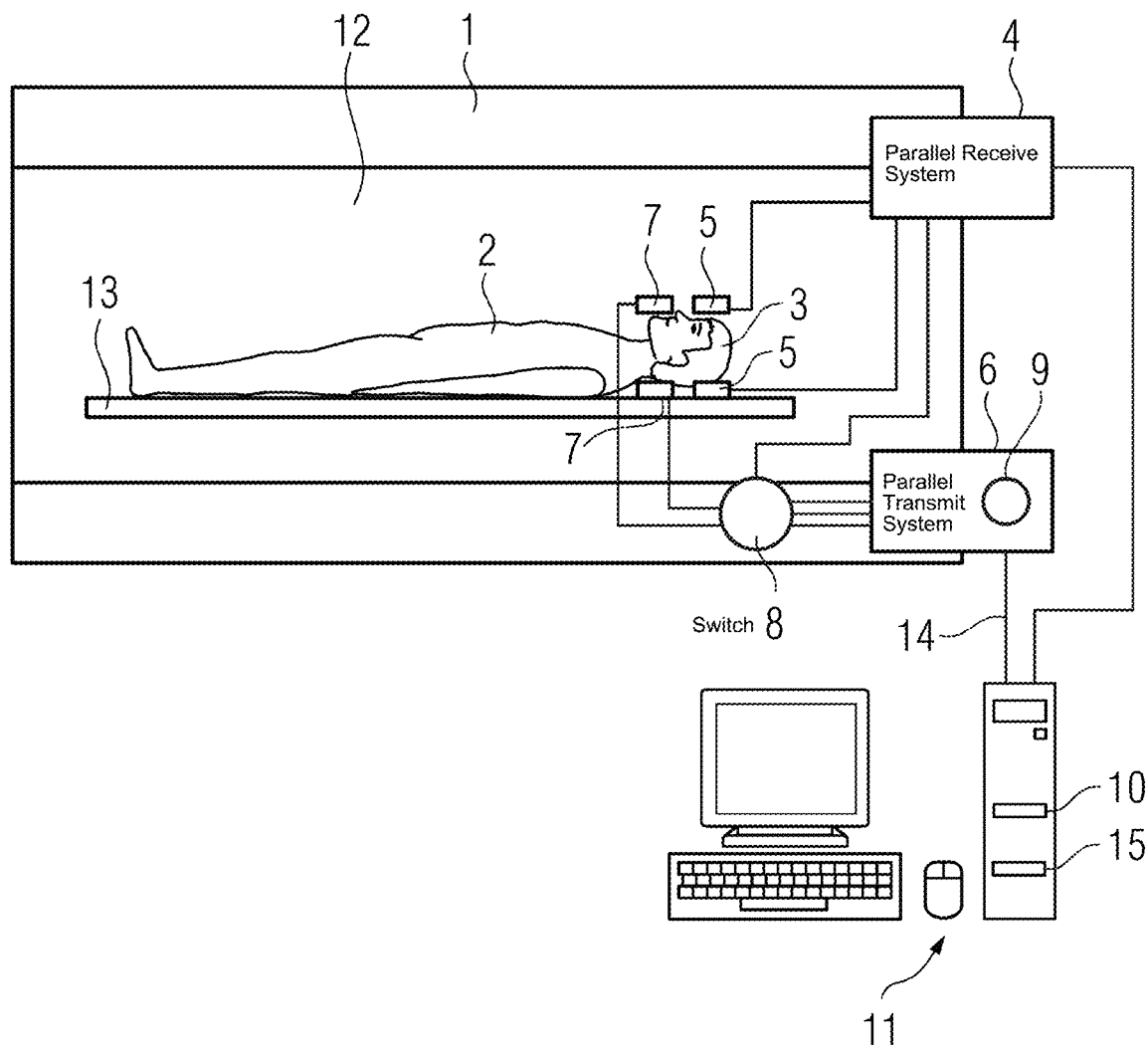
FIG. 1 shows a schematic representation of a system according to an embodiment.

FIG. 1 shows a schematic representation of one embodiment of a system. A subject is in this case a patient 2 lying on a patient support 13 inside a bore 12 of a magnetic resonance (MR) imaging device 1. The MR imaging device 1 may, for example, operate with a magnetic field of 7 Tesla (e.g., generated inside the bore 12). The bore 12 is an examination area of the MR imaging system. The part of the patient 2 that is examined in this case is, for example, the head 3 of the patient 2. An RF transmit coil array 7 as well as an RF receive coil array 5 is placed around the head 3 of the patient 2. The RF transmit coil array 7 is driven by a parallel transmit system 6, and the RF receive coil array 5 is driven by a parallel receive system 4. The parallel transmit system 6 is configured to generate MR excitation pulses that are transmitted towards the subject or part of the subject (e.g., the head 3) via the RF transmit coil array 7. The parallel receive system 4 is configured to receive magnetic resonance signals via the RF receive coil array 5. Both the parallel transmit system 6 and the parallel receive system 4 include multiple channels (not shown) for the generation and processing of signals and/or pulses, respectively (e.g., for generating and processing multiple signals and/or pulses in parallel). The system further includes a control unit 15 that is configured to prompt the parallel transmit system 6 to generate pilot tone signals and transmit the pilot tone signals via the RF transmit coil array 7. It is an option that transmit coils of the RF transmit coil array 7 that are at opposing sides of the part of the subjects (e.g., of the head 3) transmit pilot tone signals simultaneously and that the pilot tone signals are modulated such that their interference causes a stationary wave. At least one node of the stationary wave then leads to the omission of the corresponding location in the head (e.g., of the mouth area) during the analysis of movement due to there being no interference of the pilot tone signal with this part of the head (e.g., the mouth) at this location. The generation and transmission of pilot tone signals is typically carried out in time spans when no MR excitation pulses are generated. Further, the amplitude of the generated pilot tone signals may be significantly smaller than the amplitude of the average MR excitation pulses. This provides that components of the parallel receive system 4 do not overdrive due to simultaneously incoming pilot tone signals and signals due to the MR excitation pulses.

The parallel receive system 4 is also controlled by the control unit 15 and will forward received pilot tone signals to an analyzing unit 10. The analyzing unit 10 is configured to determine movement of the subject (e.g., of the head 3) by analyzing changes in the received pilot tone signal. In this embodiment, both the control unit 15 and the analyzing unit 10 are part of a computer 11 that may be controlled and/or adjusted by a user. Further, the parallel transmit system 4 includes a directional coupler 9 that is configured to separate incoming signals (e.g., reflected waves) and outgoing signals. The incoming signals are forwarded to a switch 8 that directs incoming signals from the parallel receive system 4 and incoming signals from the parallel transmit system 6 via a common signal line 14 towards the analyzing unit 10.

Figure 2:
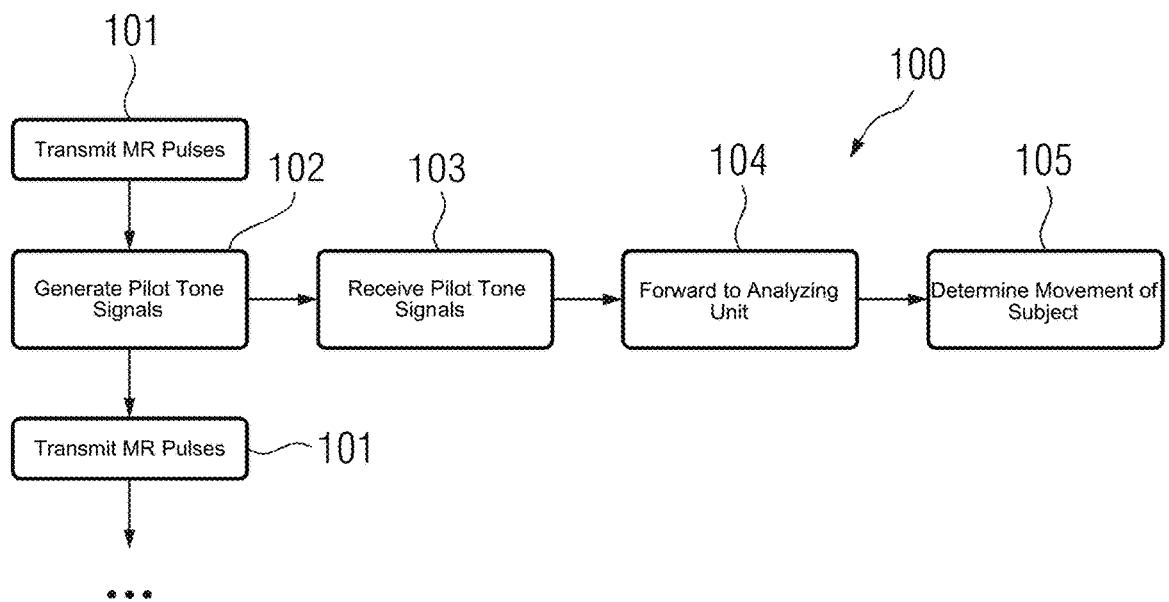
FIG. 2 shows a schematic flow diagram illustrating an embodiment of a method.

FIG. 2 shows a schematic flow diagram illustrating an embodiment of a method, where movement of at least one subject being located inside an MR imaging device is to be detected. According to an MR sequence protocol, the method includes a first act 101 of transmitting MR excitation pulses via a parallel transmit system 6 and receiving MR signals via a parallel receive system 4 during a receive time window. After the transmission of the MR excitation pulses, the following act 102 includes generating pilot tone signals (e.g., multi-channel pilot tone signals) and transmitting the pilot tone signals via the parallel transmit system. In one embodiment, an amplitude of the pilot tone signals is significantly smaller than an amplitude of average MR excitation pulses. A number of pilot tone signals may be sent in parallel, generated via parallel channels of the parallel transmit system. Therein, signal characteristics, such as frequency, phase, and/or amplitude, of the parallelly generated pilot tone signals may be modulated individually for each pilot tone signal. A number of pilot tone signals may be transmitted simultaneously or consecutively. During the transmission of the pilot tone signals, the pilot tone signals are received via an RF receive coil array of the receive system 4 in act 103 and forwarded to an analyzing unit 10 in act 104. Optionally, signal characteristics of the transmitted pilot tone signals may be shared between the parallel transmit system 6 and the parallel receive system 4 (e.g., the parallel transmit system 6 may forward information about the signal characteristics to the parallel receive system 4). The forwarding of information may, for example, be coordinated and/or initiated by the control unit 15. In act 105, the analyzing unit 10 determines movement of the subject or of at least one part of the subject by analyzing the received pilot tone signal. Thus, acts 102-105 may be summarized as movement detection acts. Therein, optionally, acts 104 and/or 105 may take place (e.g., partially take place) during the time window of act 101. The acts 102-103 are carried out in between the actual MR measurement acts 101. Thus, acts 102-103 and act 101 may alternate a number of times during an MR sequence protocol 100. Detection and encoding of the MR signal may also be carried out in between the acts 101.

Figure 3:
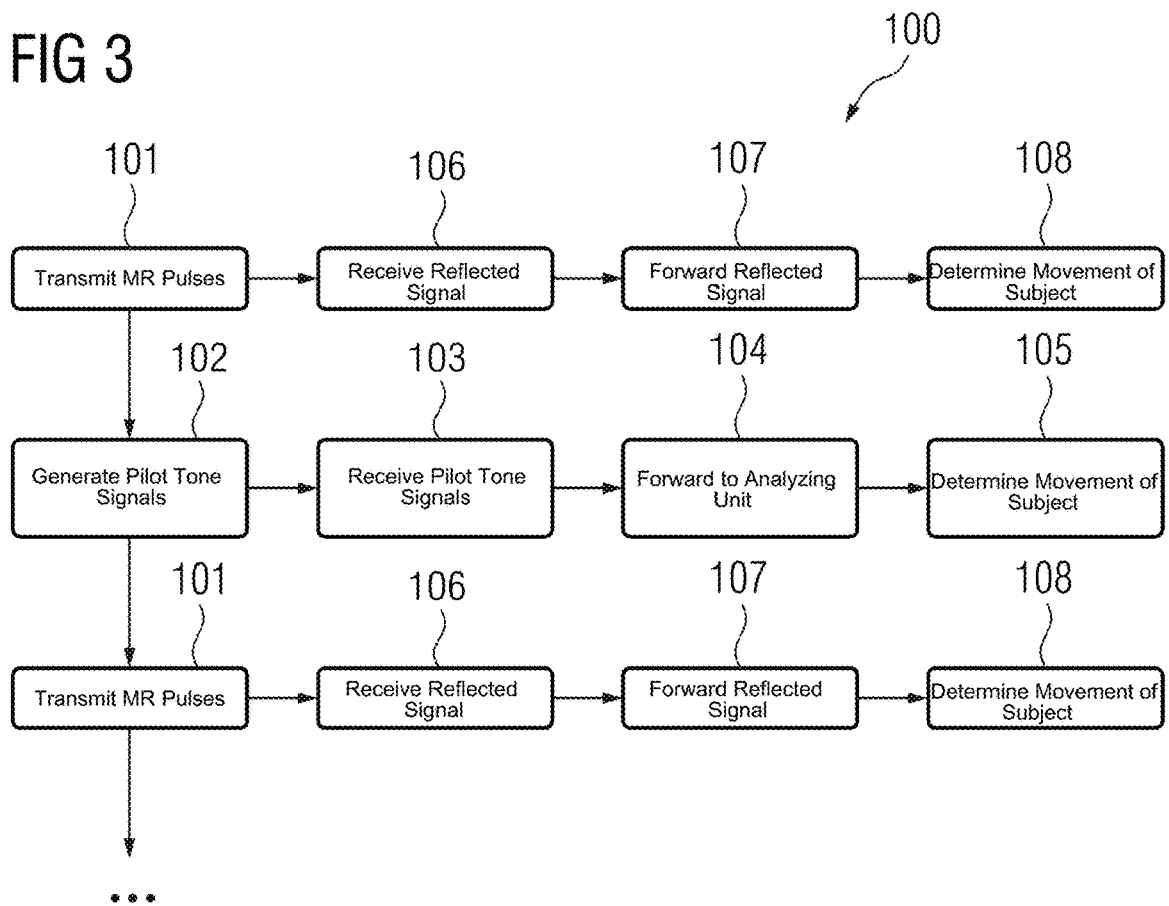
FIG. 3 shows a schematic flow diagram illustrating another embodiment of a method.

FIG. 3 shows a schematic flow diagram illustrating another embodiment of a method. This embodiment differs from the method shown in FIG. 2 due to the addition of acts 106-108. Therein, act 106 includes receiving the signal reflected during an MR excitation pulse via the parallel transmit system 6 and separating the reflected signal from the MR excitation pulse being currently transmitted by at least one directional coupler 9. The reflected signal is then forwarded to the analyzing unit 10 in act 107. In act 108, the analyzing unit 10 determines movement of the subject based on the reflected signal and, for example, based on changes of the reflected signal over time. Hence, according to this embodiment, movement of the subject is detected in between MR excitation pulses as well as during MR excitation pulses and therefore substantially continuously during the whole scan time.

Figure 4:
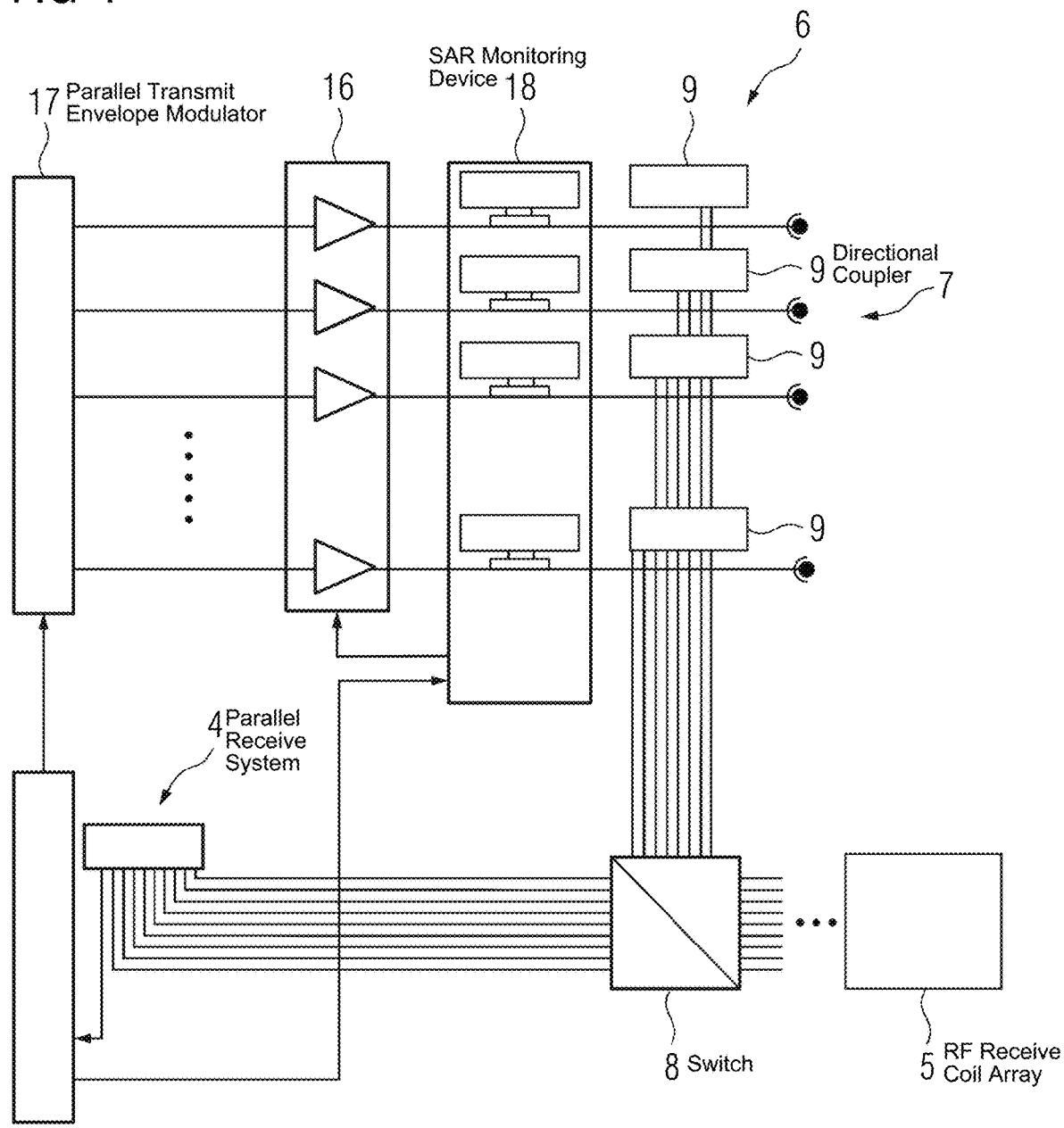
FIG. 4 shows a schematic representation of a transmit and receive system according to an embodiment.

FIG. 4 shows a schematic representation of a transmit and receive system according to an embodiment. Incoming and outgoing signals of the number of channels of the parallel transmit system 6 are separated by directional couplers 9. The incoming signals are directed to the switch 8. At a switch 8, signals from the RF receive coil array 5 are incoming from the right side and signals from RF transmit coil array via the parallel transmit system 6 are incoming from above. The switch 8 redirects all incoming signals to the parallel receive system 4. The parallel receive system 4 is configured to receive the incoming signals and process the incoming signals further. The outgoing signals (e.g., RF excitation pulses and or pilot tone signals) at the parallel transmit system 6 are generated at the parallel transmit envelope modulator 17 in parallel channels. These signals are amplified at the RF power amplifier 16. The SAR monitoring device 18 provides that the calculated SAR is always smaller than a predetermined threshold by monitoring the incoming amplitude. The individual components of the receive system 4 and the transmit system 5 may be further interconnected with each other as depicted by the arrows.

Figure 5:
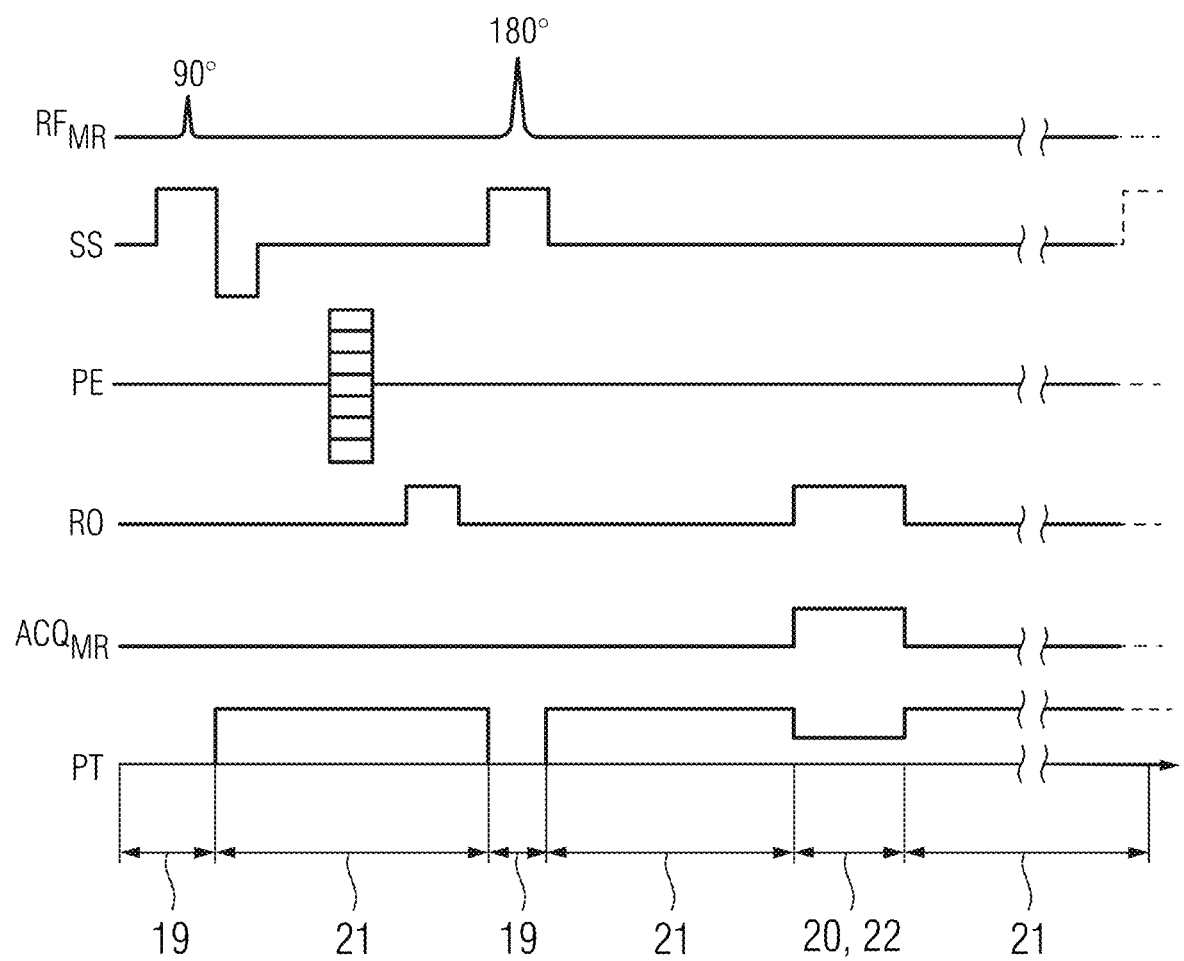
FIG. 5 shows a pulse timing diagram of an MR sequence protocol according to an embodiment.

FIG. 5 shows a pulse timing diagram of an MR sequence protocol 100 according to an embodiment. The line $RF_{MR}$ shows the sequence of RF excitation pulses that are transmitted during excitation time intervals 19. The part of the MR sequence protocol 100 that is shown here includes a 90° excitation pulse and a 180° excitation pulse. The lines labelled SS, PE, and RO represent slice selection, phase encoding, and readout dephasing gradients, respectively, that are applied in a typical MR sequence. The line labelled $ACQ_{MR}$ represents the reception of MR signals. In this example, one receive time window 20 during which MR signals are received is shown. The line labelled PT represents the simultaneous transmission and acquisition of pilot tone signals. The pilot tones are transmitted via the same parallel transmit system 6 as the RF excitation pulses and received via the same parallel receive system 4 as the MR signals. For the sake of providing a better overview, the Pilot tone signals are separated from the $RF_{MR}$ and $ACQ_{MR}$ lines. Further, the transmission and acquisition sequence are assumed to be essentially equivalent in this case and may be combined into one line (e.g., the PT line). As shown, in this example, the amplitude of the pilot tone signals is zero during the excitation time intervals 19 (e.g., no pilot tone signals are transmitted during this time). Alternatively, the amplitude of the pilot tone signals may have a value greater than zero during the excitation time intervals 19. In one embodiment, the amplitude of the pilot tone signal may be smaller (e.g., significantly smaller) than the amplitude of the MR excitation pulses in order to avoid a disturbance of the MR measurement. The receive system may be detuned and/or switched off during MR excitation intervals 19. This may provide that the signal load on the receive system 4 is not too high during the excitation time intervals 19. Otherwise, components of the receive system may overdrive if the MR excitation pulses and the pilot tone signals are transmitted simultaneously. In between the excitation time intervals 19, there are two different pilot tone time windows (e.g., a first pilot tone time window 21 that is applied in the absence of the receive time window, and a second pilot tone time window 22 that is applied during the receive time window 20). The amplitude of the pilot tone signal during the second pilot tone time window 22 is lowered with respect to the amplitude of the pilot tone signal at the first pilot tone time window 21. This may provide that the MR signal acquisition during the receive time window 20 is less disturbed due to the lower pilot tone signal at this time, potentially leading to a better signal-to-noise ratio of the MR measurement. The pilot tone signal is higher when no MR signals are measured in order to improve the signal-to-noise ratio of the measurement of the pilot tone signal during this time.

The elements and features recited in the appended claims may be combined in different ways to produce new claims that likewise fall within the scope of the present invention. Thus, whereas the dependent claims appended below depend from only a single independent or dependent claim, it is to be understood that these dependent claims may, alternatively, be made to depend in the alternative from any preceding or following claim, whether independent or dependent. Such new combinations are to be understood as forming a part of the present specification.

While the present invention has been described above by reference to various embodiments, it should be understood that many changes and modifications can be made to the described embodiments. It is therefore intended that the foregoing description be regarded as illustrative rather than limiting, and that it be understood that all equivalents and/or combinations of embodiments are intended to be included in this description.

The invention claimed is:

1. A method for detecting movement of at least one part of a subject being located inside a magnetic resonance imaging device, wherein the magnetic resonance imaging device comprises a parallel transmit system having multiple channels, the parallel transmit system being configured to transmit magnetic resonance excitation pulses via an RF transmit coil array, and a receive system that is configured to receive magnetic resonance signals via an RF receive coil, the method comprising:
performing a magnetic resonance scan, the performing of the magnetic resonance scan comprising executing a programmable magnetic resonance sequence protocol, wherein the programmable magnetic resonance sequence protocol comprises magnetic resonance excitation pulses to be transmitted via the parallel transmit system and receive time windows for receiving magnetic resonance signals via the receive system, wherein the programmable magnetic resonance sequence protocol comprises, in between the magnetic resonance excitation pulses, generation of multi-channel pilot tone signals;
transmitting the multi-channel pilot tone signals via the parallel transmit system and the RF transmit coil array;
during the transmission of the multi-channel pilot tone signals, receiving the pilot tone signals with the RF receive coil;
forwarding the received pilot tone signals via the receive system to an analyzing unit; and
determining movement of at least one part of the subject, the determining of the movement of the at least one part of the subject comprising analyzing the received pilot tone signal at the analyzing unit,
wherein the pilot tone signals have an amplitude that is 100 to 5000 times smaller than an amplitude of an average magnetic resonance excitation pulse.

2. The method of claim 1, wherein receiving the pilot tone signals with the RF receive coil comprises receiving the pilot tone signals with the RF receive coil of a parallel receive system having multiple channels.

3. The method of claim 1, wherein receiving the pilot tone signals with the RF receive coil comprises receiving the pilot tone signals with an RF receive coil array.

4. The method of claim 1, wherein the pilot tone signals have an amplitude that is 1000 to 3000 times smaller than the amplitude of the average magnetic resonance excitation pulse.

5. The method of claim 1, further comprising:
creating the pilot tone signals in multiple parallel transmit channels; and
modulating signal characteristics for each transmit channel of the multiple parallel transmit channels separately such that various pilot tone signals are created with different signal characteristics.

6. The method of claim 5, further comprising sharing the signal characteristics of the modulated pilot tone signals between the parallel transmit system and the receive system.

7. The method of claim 1, further comprising transmitting multiple of the pilot tone signals in parallel via the RF transmit coil array,
wherein the multiple pilot tone signals differ in frequency.

8. The method of claim 1, further comprising transmitting different of the pilot tone signals consecutively via different channels of the parallel transmit system.

9. The method of claim 1, further comprising:
transmitting at least two of the pilot tone signals from two transmit coils at opposing sides of the subject, both transmit coils being part of the RF transmit coil array; and
modulating the at least two pilot tone signals such that an interference pattern for the at least two pilot tone signals has at least one constant minimum at one part of the subject, from which movement is not to be taken into account.

10. The method of claim 1, further comprising:
receiving a signal reflected during a magnetic resonance excitation pulse via the parallel transmit system and separating the reflected signal from the magnetic resonance excitation pulse being currently transmitted by at least one directional coupler;
forwarding the reflected signals to the receive system and further to the analyzing unit; and
determining movement of the subject during transmission of the magnetic resonance excitation pulse, the determining of the movement of the subject during transmission of the magnetic resonance excitation pulse comprising analyzing changes in the reflected signal at the analyzing unit.

11. The method of claim 1, wherein determining the movement of the subject during transmission of the magnetic resonance excitation pulse further comprises determining the movement of the subject during transmission of the magnetic resonance excitation pulse using a scatter matrix for analyzing the received pilot tone signals.

12. The method of claim 1, further comprising calculating a specific adsorption rate (SAR) of the subject, the calculating comprising adding a constant safety factor due to the pilot tone signal within a general SAR model.

13. A magnetic resonance imaging system configured to detect movement of at least a part of a subject, the part of the subject being located inside an examination area of the magnetic resonance imaging system, the magnetic resonance imaging system comprising:
a parallel transmit system having multiple channels, the parallel transmit system being configured to generate and transmit magnetic resonance excitation pulses via a radio frequency (RF) transmit coil array;

a receive system having multiple channels, the receive system being configured to receive magnetic resonance signals via an RF receive coil; and a control unit comprising an analyzing unit, wherein the control unit is configured to:
- prompt the parallel transmit system to generate and transmit pilot tone signals according to a sequence protocol in between the transmission of magnetic resonance excitation pulses; and
- prompt the receive system to receive pilot tone signals and forward the received pilot tone signals to the analyzing unit, wherein the analyzing unit is configured to determine movement of the subject, the determination of the movement of the subject comprising analyzing changes in the received pilot tone signal, and wherein the parallel transmit system is configured such that a signal path in the parallel transmit system is linear at signal amplitudes of about 0.02V to 0.5V.

14. The magnetic resonance imaging system of claim 13, wherein the receive system is a parallel receive system.

15. The magnetic resonance imaging system of claim 13, wherein the parallel transmit system is configured such that the signal path in the parallel transmit system is linear at signal amplitudes of about 0.01V to 1V.

16. The magnetic resonance imaging system of claim 13, wherein the RF transmit coil array and the RF receive coil are integrated into one local coil that is configured to be placed adjacent to the part of the subject inside the magnetic resonance imaging device.

17. The system of claim 13, wherein signal generating elements of the parallel transmit system comprise at least one directional coupler, wherein the at least one directional coupler is configured to:
- separate incoming signals that are incoming at the RF transmit coil array and outgoing signals that are currently transmitted from the RF transmit coil array; and
- forward the incoming signals to the receive system.

18. In a non-transitory computer-readable storage medium that stores instructions executable by a control unit connected to a magnetic resonance imaging device or part of the magnetic resonance imaging device to detect movement of at least one part of a subject being located inside the magnetic resonance imaging device, wherein the magnetic resonance imaging device comprises a parallel transmit system having multiple channels, the parallel transmit system being configured to transmit magnetic resonance excitation pulses via an RF transmit coil array, and a receive system that is configured to receive magnetic resonance signals via an RF receive coil, the instructions comprising:

performing a magnetic resonance scan, the performing of the magnetic resonance scan comprising executing a programmable magnetic resonance sequence protocol, wherein the programmable magnetic resonance sequence protocol comprises magnetic resonance excitation pulses to be transmitted via the parallel transmit system and receive time windows for receiving magnetic resonance signals via the receive system, wherein the programmable magnetic resonance sequence protocol comprises, in between the magnetic resonance excitation pulses, generation of multi-channel pilot tone signals;

transmitting the multi-channel pilot tone signals via the parallel transmit system and the RF transmit coil array;

during the transmission of the multi-channel pilot tone signals, receiving the pilot tone signals with the RF receive coil;

forwarding the received pilot tone signals via the receive system to an analyzing unit; and determining movement of at least one part of the subject, the determining of the movement of the at least one part of the subject comprising analyzing the received pilot tone signal at the analyzing unit, wherein the pilot tone signals have an amplitude that is 100 to 5000 times smaller than an amplitude of an average magnetic resonance excitation pulse.

* * * * *